(12) United States Patent
Dehesh et al.

(10) Patent No.: US 6,483,008 B1
(45) Date of Patent: *Nov. 19, 2002

(54) METHODS FOR PRODUCING PLANTS WITH ELEVATED OLEIC ACID CONTENT

(75) Inventors: Katayoon Dehesh, Vacaville, CA (US); Vic C. Knauf, Bainbridge Island, WA (US); Gregory A. Thompson, Clarkston, WA (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/304,603

(22) Filed: May 3, 1999

Related U.S. Application Data

(63) Continuation-in-part of application No. 07/987,256, filed on Dec. 7, 1992, now Pat. No. 6,348,642, which is a continuation-in-part of application No. 07/568,493, filed on Aug. 15, 1990, now abandoned.

(51) Int. Cl.[7] .......................... A01H 5/00; C12N 15/82
(52) U.S. Cl. ...................... 800/281; 800/298; 800/286; 435/419; 536/23.6
(58) Field of Search .................. 800/281, 286, 800/298; 435/69.1, 419; 536/23.6

(56) References Cited

U.S. PATENT DOCUMENTS 5,510,255 A * 4/1996 Knauf ...................... 435/172.3
5,850,026 A * 12/1998 Debonte et al.

FOREIGN PATENT DOCUMENTS

| WO | WO92/03564 A | * | 3/1992 |
| WO | WO93/10240 A | * | 5/1993 |
| WO | WO94/10189 A | * | 5/1994 |
| WO | WO97/40698 | * | 11/1997 |
| WO | WO98/46776 A | * | 10/1998 |

OTHER PUBLICATIONS

Van de Loo et al, "An oleate 12–hydroxylase from *Ricinus communis*L. is a fatty acyl desaturase homolog", Jul. 1995, Proc. Natl. Acad. Sci. vol. 92 pp. 6743–6747.*
Broun et al, "Catalytic Plasicity of Fatty Acid Modification Enzymes nderlying Chemical Diversity of Plant Lipids" Nov. 1998, Science vol. 282 pp. 1315–1317.*
Bork, "Go hunting in sequence databases but watch out for the traps", Oct. 1996, vol. 12 No. 10 pp. 425–427.*
Brenner, "Errors in genome annotation", Apr. 1999 TIG vol. 15 No. 4 pp. 132–133.*
Smith et al, The challenges of genome sequence annotation or "The devil is in the details", Nov. 1997 Nature Biotechnology vol. 15 pp. 1222–1223.*
Doerks et al, "Protein annotation: detective work for function prediction", Jun. 1998, TIG vol. 14 No. 6 pp.248–250.*
Notification of Transmittal of International Search Report & International Search Report for PCT/US00/12377 (Mar. 8, 2001).*
Kinney et al., "Stearoyl–ACP desaturase and a beta ketoacyl–ACP synthetase from developing soybean seeds", Plant Lipid Biochemistry, 126–28 (1990) In Plant Lipid Biochemistry (Quinn et al, eds) Portland Press Ltd, London, England, U.K.*
EMBL Accession No. AF243182 (Apr. 5, 2000).*
EMBL Accession No. AF244518 (Apr. 5, 2000).*

* cited by examiner

*Primary Examiner*—Elizabeth F. McElwain
(74) *Attorney, Agent, or Firm*—Arnold & Porter; Alissa M. Eagle

(57) ABSTRACT

By this invention, methods to produce oleic fatty acids in plant seed oils are provided. The methods of the present invention generally involve the suppression of a host plant cells endogenous β-ketoacyl-ACP synthase I protein. Also described in the instant invention are the plants, cells and oils obtained therefrom.

13 Claims, 3 Drawing Sheets

| | STRAIN ID | 12:0 | 14:0 | 16:0 | 16:1 | 18:0 | 18:1_C9 | 18:2_C9,12 | 18:3_C9,12,15 | 20:0 | 20:1 | 20:2 | 22:0 | 22:1 | 22:2 |
|---|---|---|---|---|---|---|---|---|---|---|---|---|---|---|---|
| 1 | 3259-D-5 | 0.03 | 0.09 | 4.74 | 0.12 | 1.52 | 55.9 | 25.85 | 10 | 0.52 | 0.94 | 0.07 | 0.19 | 0.01 | 0 |
| 2 | 3259-D-5 | 0.02 | 0.08 | 4.4 | 0.13 | 1.28 | 52.9 | 26.62 | 12.58 | 0.43 | 1.21 | 0.1 | 0.23 | 0.01 | 0 |
| 3 | 3259-D-5 | 0.01 | 0.08 | 4.36 | 0.18 | 1.73 | 53.31 | 27.72 | 10.72 | 0.58 | 0.96 | 0.07 | 0.27 | 0.01 | 0 |
| 4 | 3259-D-5 | 0.01 | 0.07 | 4.18 | 0.15 | 1.4 | 48.72 | 31.5 | 12.42 | 0.41 | 0.92 | 0.07 | 0.13 | 0 | 0 |
| 5 | 3259-D-5 | 0.01 | 0.08 | 4.19 | 0.12 | 1.17 | 59.63 | 20.67 | 11.89 | 0.45 | 1.48 | 0.09 | 0.19 | 0 | 0.01 |
| 6 | 3259-D-5 | 0.01 | 0.08 | 4.36 | 0.12 | 0.99 | 56.32 | 22.85 | 13.47 | 0.38 | 1.14 | 0.09 | 0.16 | 0.01 | 0 |
| 7 | 3259-D-5 | 0.01 | 0.09 | 4.65 | 0.14 | 1.27 | 62.48 | 21.95 | 7.77 | 0.47 | 0.96 | 0.09 | 0.13 | 0 | 0 |
| 8 | 3259-D-5 | 0.02 | 0.08 | 4.13 | 0.13 | 1.18 | 61.88 | 21.18 | 9.5 | 0.45 | 1.13 | 0.08 | 0.24 | 0 | 0 |
| 9 | 3259-D-5 | 0.01 | 0.09 | 4.58 | 0.12 | 2.23 | 62.08 | 23.96 | 4.43 | 0.73 | 1.36 | 0.08 | 0.32 | 0 | 0 |
| 10 | 3259-D-5 | 0.01 | 0.08 | 4.19 | 0.15 | 1.35 | 59.59 | 23.65 | 9.09 | 0.49 | 1.06 | 0.1 | 0.24 | 0.01 | 0 |
| 11 | 3259-D-5 | 0.01 | 0.07 | 3.6 | 0.08 | 1.7 | 69.37 | 15.51 | 7.25 | 0.59 | 1.48 | 0.08 | 0.26 | 0 | 0 |
| 12 | 3259-D-5 | 0.02 | 0.09 | 4.28 | 0.12 | 1.6 | 53.61 | 29.73 | 8.69 | 0.46 | 1.13 | 0.1 | 0.17 | 0 | 0 |
| 13 | 3259-D-5 | 0.01 | 0.08 | 4.17 | 0.12 | 2.2 | 62.92 | 21.14 | 6.91 | 0.69 | 1.41 | 0.07 | 0.27 | 0.01 | 0 |
| 14 | 3259-D-5 | 0.02 | 0.13 | 5.47 | 0.28 | 1.21 | 52.36 | 32.04 | 6.62 | 0.48 | 1.09 | 0.1 | 0.2 | 0 | 0 |
| 15 | 3259-D-5 | 0.02 | 0.07 | 4.37 | 0.2 | 1.33 | 64.37 | 19.45 | 8.16 | 0.44 | 1.31 | 0.07 | 0.19 | 0 | 0 |
| 16 | 3259-D-5 | 0.01 | 0.08 | 4.12 | 0.13 | 1.93 | 66.88 | 19.03 | 5.26 | 0.66 | 1.56 | 0.1 | 0.24 | 0 | 0 |
| 17 | 3259-D-5 | 0.01 | 0.09 | 4.23 | 0.14 | 1.17 | 56.83 | 26.45 | 9.3 | 0.37 | 1.16 | 0.1 | 0.15 | 0 | 0 |
| 18 | 3259-D-5 | 0.01 | 0.1 | 5 | 0.24 | 1.03 | 50.98 | 31.03 | 9.86 | 0.37 | 1.11 | 0.1 | 0.14 | 0.02 | 0 |
| 19 | 3259-D-5 | 0.01 | 0.09 | 4.38 | 0.11 | 1.12 | 51.25 | 30.23 | 11.13 | 0.37 | 1.08 | 0.12 | 0.09 | 0.01 | 0 |
| 20 | 3259-D-5 | 0.01 | 0.09 | 4.3 | 0.08 | 1.36 | 47.18 | 30.81 | 14.74 | 0.33 | 1 | 0.1 | 0 | 0.01 | 0 |
| 21 | 3259-D-5 | 0.01 | 0.08 | 3.75 | 0.08 | 1.34 | 60.41 | 22.21 | 10.22 | 0.47 | 1.2 | 0.12 | 0.1 | 0 | 0 |
| 22 | 3259-D-5 | 0.01 | 0.08 | 4.43 | 0.15 | 1.45 | 64.51 | 19.35 | 7.83 | 0.53 | 1.37 | 0.06 | 0.24 | 0 | 0 |
| 23 | 3259-D-5 | 0.02 | 0.11 | 4.48 | 0.15 | 1.4 | 52.87 | 26.6 | 12.63 | 0.46 | 0.99 | 0.11 | 0.18 | 0 | 0 |
| 24 | 3259-D-5 | 0.02 | 0.07 | 4.25 | 0.12 | 1.53 | 65.95 | 18.24 | 7.85 | 0.53 | 1.18 | 0 | 0.26 | 0.01 | 0 |
| 25 | 3259-D-5 | 0.01 | 0.08 | 3.93 | 0.08 | 2.3 | 69.76 | 17.1 | 4.29 | 0.71 | 1.36 | 0.08 | 0.27 | 0.01 | 0 |
| 26 | 3259-D-5 | 0.02 | 0.1 | 4.91 | 0.22 | 1.66 | 52.88 | 30.66 | 8 | 0.46 | 0.84 | 0.07 | 0.19 | 0 | 0 |
| 27 | 3259-D-5 | 0.01 | 0.06 | 4.2 | 0.1 | 1.34 | 62.23 | 19.52 | 10.38 | 0.48 | 1.29 | 0.08 | 0.29 | 0.01 | 0 |
| 28 | 3259-D-5 | 0.01 | 0.09 | 4.95 | 0.18 | 1.13 | 56.04 | 24.75 | 10.79 | 0.45 | 1.31 | 0.09 | 0.19 | 0.02 | 0 |
| 29 | 3259-D-5 | 0.01 | 0.07 | 4.42 | 0.12 | 1.23 | 62.59 | 18.92 | 10.48 | 0.5 | 1.38 | 0.06 | 0.22 | 0 | 0 |
| 30 | 3259-D-5 | 0.01 | 0.09 | 4.74 | 0.25 | 1.04 | 51.92 | 26.87 | 13.47 | 0.34 | 1.03 | 0.07 | 0.11 | 0 | 0 |
| 31 | 3259-D-5 | 0.01 | 0.09 | 4.49 | 0.13 | 1.19 | 58.52 | 23.66 | 10.06 | 0.42 | 1.22 | 0.1 | 0.12 | 0.01 | 0 |
| 32 | 3259-D-5 | 0.01 | 0.09 | 4.79 | 0.21 | 1.75 | 58.68 | 24.9 | 7.54 | 0.53 | 1.21 | 0.07 | 0.2 | 0.02 | 0 |
| 33 | 3259-D-5 | 0.01 | 0.08 | 4.02 | 0.12 | 2.51 | 64.67 | 19.33 | 6.89 | 0.71 | 1.34 | 0.07 | 0.26 | 0.01 | 0 |
| 34 | 3259-D-5 | 0.01 | 0.08 | 4.47 | 0.12 | 1.46 | 62.06 | 20.79 | 8.85 | 0.5 | 1.36 | 0.08 | 0.21 | 0 | 0 |

Figure 1/1

| # | ID | | | | | | | | | | | | | |
|---|---|---|---|---|---|---|---|---|---|---|---|---|---|---|
| 35 | 3259-D-5 | 0.01 | 0.09 | 4.33 | 0.12 | 1.07 | 49.48 | 29.88 | 13.11 | 0.34 | 1.31 | 0.11 | 0.1 | 0.01 | 0 |
| 36 | 3259-D-5 | 0.01 | 0.07 | 3.99 | 0.08 | 1.85 | 64.37 | 19.67 | 7.5 | 0.6 | 1.41 | 0.08 | 0.35 | 0 | 0 |
| 37 | 3259-D-5 | 0.01 | 0.09 | 4.21 | 0.16 | 2.62 | 60.45 | 22.54 | 7.54 | 0.76 | 1.27 | 0.06 | 0.3 | 0 | 0 |
| 38 | 3259-D-5 | 0.01 | 0.1 | 4.99 | 0.28 | 1.19 | 50.64 | 27.81 | 13.04 | 0.43 | 1.19 | 0.1 | 0.21 | 0 | 0 |
| 39 | 3259-D-5 | 0.01 | 0.09 | 3.7 | 0.06 | 2.51 | 70.93 | 15.04 | 5.1 | 0.73 | 1.36 | 0.1 | 0.36 | 0 | 0 |
| 40 | 3259-D-5 | 0.02 | 0.07 | 4.2 | 0.12 | 2.21 | 63.71 | 20.51 | 7.06 | 0.64 | 1.16 | 0.06 | 0.26 | 0 | 0 |
| 41 | 3259-D-5 | 0.03 | 0.07 | 4.56 | 0.1 | 4.58 | 67.39 | 16.77 | 4.1 | 1.16 | 1.22 | 0 | 0 | 0.01 | 0 |
| 42 | 3259-D-5 | 0.02 | 0.11 | 5.68 | 0.36 | 0.98 | 38 | 34.92 | 16.02 | 0.38 | 1.09 | 0.12 | 0.23 | 0 | 0.01 |
| 43 | 3259-D-5 | 0.02 | 0.08 | 4.33 | 0.14 | 1.47 | 57.52 | 26.51 | 8.03 | 0.44 | 1.27 | 0.09 | 0.11 | 0.01 | 0 |
| 44 | 3259-D-5 | 0.01 | 0.1 | 4.61 | 0.16 | 1.21 | 42.24 | 37.08 | 13.22 | 0.36 | 0.76 | 0.15 | 0.09 | 0 | 0 |
| 45 | 3259-D-5 | 0.01 | 0.1 | 4.43 | 0.17 | 1.91 | 65.33 | 21.13 | 4.51 | 0.66 | 1.44 | 0.07 | 0.24 | 0 | 0 |
| 46 | 3259-D-5 | 0.01 | 0.08 | 4.28 | 0.14 | 1.2 | 62.88 | 18.83 | 10.37 | 0.5 | 1.42 | 0 | 0.27 | 0 | 0 |
| 47 | 3259-D-5 | 0.02 | 0.07 | 3.71 | 0.08 | 1.4 | 63.62 | 21.07 | 7.97 | 0.46 | 1.33 | 0.12 | 0.14 | 0.01 | 0 |
| 48 | 3259-D-5 | 0.01 | 0.08 | 4.45 | 0.12 | 2.02 | 58.81 | 24.02 | 8.35 | 0.69 | 1.11 | 0.08 | 0.26 | 0.01 | 0 |
| 49 | 3259-D-5 | 0.02 | 0.12 | 4.04 | 0.1 | 1.88 | 60.85 | 22.09 | 8.83 | 0.57 | 1.08 | 0.1 | 0.27 | 0 | 0 |
| 50 | 3259-D-5 | 0.02 | 0.06 | 4.79 | 0.17 | 1.55 | 56.32 | 29.83 | 5.19 | 0.54 | 1.12 | 0.12 | 0.24 | 0 | 0 |
| 51 | 3259-D-12 | 0.01 | 0.07 | 4.02 | 0.09 | 1.57 | 70.55 | 12.5 | 8.61 | 0.69 | 1.4 | 0.06 | 0.43 | 0 | 0 |
| 52 | 3259-D-12 | 0.01 | 0.06 | 4.36 | 0.09 | 1.96 | 66.33 | 17.81 | 6.73 | 0.84 | 1.21 | 0.06 | 0.52 | 0 | 0 |
| 53 | 3259-D-12 | 0.01 | 0.12 | 4.19 | 0.09 | 2.08 | 67.2 | 15.17 | 8.27 | 0.88 | 1.46 | 0.07 | 0.51 | 0.01 | 0 |
| 54 | 3259-D-12 | 0.01 | 0.09 | 4.73 | 0.09 | 1.46 | 68.84 | 12.97 | 8.87 | 0.7 | 1.69 | 0.08 | 0.44 | 0 | 0 |
| 55 | 3259-D-12 | 0.01 | 0.07 | 4.17 | 0.08 | 1.65 | 65.93 | 17.54 | 7.78 | 0.75 | 1.45 | 0.07 | 0.44 | 0 | 0 |
| 56 | 3259-D-12 | 0.01 | 0.06 | 3.96 | 0.09 | 1.33 | 68.07 | 14.26 | 9.93 | 0.57 | 1.35 | 0.07 | 0.3 | 0.01 | 0 |
| 57 | 3259-D-12 | 0.01 | 0.06 | 3.88 | 0.09 | 1.55 | 73.99 | 10.14 | 7.65 | 0.69 | 1.5 | 0.05 | 0.39 | 0 | 0 |
| 58 | 3259-D-12 | 0.01 | 0.06 | 3.7 | 0.07 | 1.7 | 73.25 | 10.49 | 8.04 | 0.74 | 1.48 | 0.05 | 0.42 | 0.01 | 0 |
| 59 | 3259-D-12 | 0.01 | 0.07 | 4.01 | 0.07 | 2.55 | 70.82 | 13.96 | 5.48 | 1.02 | 1.49 | 0 | 0.52 | 0 | 0 |
| 60 | 3259-D-12 | 0.01 | 0.06 | 3.81 | 0.07 | 1.72 | 73.95 | 10.7 | 6.85 | 0.71 | 1.67 | 0.05 | 0.38 | 0.01 | 0 |
| 61 | 3259-D-12 | 0.01 | 0.07 | 3.66 | 0.06 | 1.63 | 73.87 | 9.29 | 8.71 | 0.72 | 1.52 | 0.05 | 0.4 | 0 | 0 |
| 62 | 3259-D-12 | 0.01 | 0.06 | 3.72 | 0.07 | 2 | 74.08 | 11.24 | 5.89 | 0.8 | 1.63 | 0.07 | 0.43 | 0 | 0 |
| 63 | 3259-D-12 | 0.01 | 0.07 | 4.16 | 0.08 | 1.97 | 70.59 | 13.03 | 7.03 | 0.89 | 1.61 | 0.06 | 0.53 | 0 | 0 |
| 64 | 3259-D-12 | 0.01 | 0.06 | 3.7 | 0.05 | 2.36 | 76.06 | 8.56 | 6.05 | 0.97 | 1.62 | 0.05 | 0.49 | 0 | 0 |
| 65 | 3259-D-12 | 0.01 | 0.06 | 3.78 | 0.07 | 2.53 | 75.32 | 9.63 | 5.15 | 1.04 | 1.78 | 0.05 | 0.56 | 0 | 0 |
| 66 | 3259-D-12 | 0.02 | 0.07 | 3.97 | 0.05 | 2.98 | 74.17 | 10.54 | 4.54 | 1.2 | 1.84 | 0.03 | 0.6 | 0 | 0 |
| 67 | 3259-D-12 | 0.01 | 0.08 | 4.32 | 0.13 | 1.47 | 65.8 | 15.69 | 9.73 | 0.71 | 1.49 | 0.09 | 0.48 | 0 | 0 |

Figure 1/2

| | | | | | | | | | | | | | | |
|---|---|---|---|---|---|---|---|---|---|---|---|---|---|---|
| 68 | 3259-D-12 | 0.01 | 0.08 | 3.93 | 0.08 | 1.63 | 63.93 | 18.08 | 9.31 | 0.73 | 1.73 | 0.09 | 0.38 | 0 | 0 |
| 69 | 3259-D-12 | 0.01 | 0.1 | 4.32 | 0.16 | 1.55 | 57.94 | 18.89 | 14.52 | 0.68 | 1.37 | 0.09 | 0.37 | 0 | 0 |
| 70 | 3259-D-12 | 0.01 | 0.07 | 3.74 | 0.05 | 2.93 | 76.68 | 8.48 | 4.56 | 1.26 | 1.56 | 0.03 | 0.62 | 0.01 | 0 |
| 71 | 3259-D-12 | 0.01 | 0.07 | 3.71 | 0.06 | 2.38 | 74.15 | 11.3 | 5.12 | 0.94 | 1.73 | 0 | 0.5 | 0.01 | 0.01 |
| 72 | 3259-D-12 | 0.02 | 0.07 | 4.27 | 0.09 | 2.04 | 66.68 | 15.27 | 8.81 | 0.81 | 1.41 | 0.06 | 0.45 | 0.01 | 0 |
| 73 | 3259-D-12 | 0.01 | 0.06 | 3.86 | 0.06 | 2.65 | 73.79 | 10.34 | 5.98 | 1.06 | 1.59 | 0.06 | 0.53 | 0 | 0 |
| 74 | 3259-D-12 | 0.02 | 0.09 | 4.42 | 0.19 | 1.83 | 62.32 | 19.81 | 8.64 | 0.72 | 1.53 | 0.06 | 0.37 | 0 | 0 |
| 75 | 3259-D-12 | 0.01 | 0.06 | 3.92 | 0.08 | 2.28 | 71.48 | 12.62 | 6.77 | 0.9 | 1.38 | 0.05 | 0.44 | 0 | 0 |
| 76 | 3259-D-12 | 0.02 | 0.1 | 4.28 | 0.09 | 1.62 | 66.55 | 16.75 | 8.04 | 0.72 | 1.39 | 0.05 | 0.38 | 0.01 | 0 |
| 77 | 3259-D-12 | 0.02 | 0.12 | 5.26 | 0.29 | 1.08 | 48.95 | 25.88 | 16.1 | 0.45 | 1.45 | 0.1 | 0.26 | 0 | 0 |
| 78 | 3259-D-12 | 0.01 | 0.07 | 4.04 | 0.07 | 1.8 | 70.21 | 12.59 | 8.71 | 0.78 | 1.37 | 0.04 | 0.3 | 0 | 0 |
| 79 | 3259-D-12 | 0.01 | 0.08 | 4.12 | 0.09 | 2.15 | 66.19 | 16.51 | 7.74 | 0.89 | 1.67 | 0.06 | 0.5 | 0 | 0 |
| 80 | 3259-D-12 | 0.01 | 0.07 | 4.01 | 0.06 | 2.41 | 73.08 | 11.19 | 5.77 | 0.99 | 1.79 | 0.06 | 0.54 | 0 | 0.01 |
| 81 | 3259-D-12 | 0.02 | 0.08 | 4.1 | 0.1 | 2.53 | 69.78 | 13.3 | 7.04 | 1.02 | 1.41 | 0.08 | 0.54 | 0 | 0 |
| 82 | 3259-D-12 | 0.01 | 0.07 | 3.96 | 0.07 | 1.86 | 67.91 | 14.86 | 8.65 | 0.77 | 1.36 | 0.08 | 0.41 | 0 | 0 |
| 83 | 3259-D-12 | 0.01 | 0.08 | 3.86 | 0.11 | 2.62 | 70.46 | 14.3 | 5.71 | 0.96 | 1.38 | 0.05 | 0.44 | 0.02 | 0 |
| 84 | 3259-D-12 | 0.01 | 0.07 | 3.97 | 0.07 | 2.21 | 72.94 | 11.03 | 6.93 | 0.94 | 1.32 | 0 | 0.51 | 0 | 0 |
| 85 | 3259-D-12 | 0.01 | 0.09 | 4.56 | 0.06 | 2.21 | 75.49 | 9.07 | 5.13 | 1.03 | 1.58 | 0.06 | 0.69 | 0 | 0 |
| 86 | 3259-D-12 | 0.01 | 0.08 | 4.31 | 0.07 | 2.38 | 72.79 | 11.07 | 6.1 | 1.04 | 1.47 | 0.08 | 0.58 | 0 | 0.01 |
| 87 | 3259-D-12 | 0.01 | 0.07 | 4.27 | 0.09 | 2.04 | 68.97 | 13.13 | 8.5 | 0.9 | 1.44 | 0.06 | 0.52 | 0 | 0 |
| 88 | 3259-D-12 | | | | | | | 0 | | | | | | | |
| 89 | 3259-D-12 | 0.01 | 0.06 | 3.8 | 0.07 | 1.91 | 75.27 | 8.94 | 7.02 | 0.82 | 1.61 | 0 | 0.48 | 0 | 0.01 |
| 90 | 3259-D-12 | 0.01 | 0.07 | 4.11 | 0.08 | 1.76 | 71.23 | 13.1 | 6.92 | 0.77 | 1.48 | 0.06 | 0.41 | 0 | 0 |
| 91 | 3259-D-12 | 0.01 | 0.07 | 3.82 | 0.06 | 1.93 | 74.41 | 10.25 | 6.32 | 0.86 | 1.76 | 0 | 0.5 | 0 | 0 |
| 92 | 3259-D-12 | 0.01 | 0.08 | 4.37 | 0.07 | 2.7 | 72.33 | 11.04 | 6.12 | 1.11 | 1.52 | 0.05 | 0.58 | 0 | 0 |
| 93 | 3259-D-12 | 0.01 | 0.1 | 4.35 | 0.12 | 2.04 | 62.74 | 20.05 | 7.78 | 0.84 | 1.36 | 0.07 | 0.53 | 0 | 0 |
| 94 | 3259-D-12 | 0.01 | 0.08 | 4.25 | 0.15 | 1.87 | 63.69 | 14.92 | 12.64 | 0.71 | 1.28 | 0.07 | 0.31 | 0 | 0 |
| 95 | 3259-D-12 | 0.01 | 0.07 | 3.88 | 0.06 | 3.67 | 69.57 | 12.16 | 6.9 | 1.3 | 1.67 | 0.06 | 0.63 | 0.02 | 0 |
| 96 | 3259-D-12 | 0.01 | 0.08 | 4.15 | 0.1 | 1.52 | 70.42 | 13.73 | 7.38 | 0.68 | 1.5 | 0.06 | 0.37 | 0.01 | 0 |
| 97 | 3259-D-12 | 0.01 | 0.1 | 3.92 | 0.05 | 1.74 | 77.86 | 8.39 | 5.02 | 0.74 | 1.79 | 0.03 | 0.35 | 0 | 0 |
| 98 | 3259-D-12 | 0.01 | 0.07 | 3.98 | 0.07 | 3.31 | 68.15 | 13.87 | 7.33 | 1.15 | 1.38 | 0.06 | 0.6 | 0 | 0 |
| 99 | 3259-D-12 | 0.01 | 0.07 | 4.08 | 0.1 | 1.52 | 71.53 | 12.83 | 7.07 | 0.68 | 1.61 | 0.05 | 0.44 | 0 | 0 |
| 100 | 3259-D-12 | 0.02 | 0.08 | 4.03 | 0.05 | 2.79 | 78.31 | 7.79 | 3.47 | 1.13 | 1.72 | 0.05 | 0.57 | 0 | 0 |

Figure 1/3

METHODS FOR PRODUCING PLANTS WITH ELEVATED OLEIC ACID CONTENT

This application is a continuation-in-part of application Ser. No. 07/987,256 filed Dec. 7, 1992, now U.S. Pat. No. 6,348,642 which is a continuation-in-part of application Ser. No. 07/568,493 filed Aug. 15, 1990, now abandoned.

FIELD OF INVENTION

The present invention is directed to methods for the increased production of particular fatty acids in plants. In particular, the present invention is directed to methods for increasing oleic acid in plants.

INTRODUCTION

BACKGROUND

Plant oils are used in a variety of industrial and edible uses. Novel vegetable oils compositions and/or improved means to obtain oils compositions, from biosynthetic or natural plant sources, are needed. Depending upon the intended oil use, various different fatty acid compositions are desired.

For example, in some instances having an oilseed with a higher ratio of oil to seed meal would be useful to obtain a desired oil at lower cost. This would be typical of a high value oil product. In some instances, having an oilseed with a lower ratio of oil to seed meal would be useful to lower caloric content. In other uses, edible plant oils with a higher percentage of unsaturated fatty acids are desired for cardiovascular health reasons. And alternatively, temperate substitutes for high saturate tropical oils such as palm and coconut, would also find uses in a variety of industrial and food applications.

One means postulated to obtain such oils and/or modified fatty acid compositions is through the genetic engineering of plants. However, in order to genetically engineer plants one must have in place the means to transfer genetic material to the plant in a stable and heritable manner. Additionally, one must have nucleic acid sequences capable of producing the desired phenotypic result, regulatory regions capable of directing the correct application of such sequences, and the like. Moreover, it should be appreciated that in order to produce a desired phenotype requires that the Fatty Acid Synthetase (FAS) pathway of the plant is modified to the extent that the ratios of reactants are modulated or changed.

Higher plants appear to synthesize fatty acids via a common metabolic pathway. In developing seeds, where fatty acids are attached to glycerol backbones, forming triglycerides, are stored as a source of energy for further germination, the FAS pathway is located in the proplastids. The first committed step is the formation of acetyl-ACP (acyl carrier protein) from acety-CoA and ACP catalyzed by the enzyme, acetyl-CoA:ACP transacylase (ATA). Elongation of acetyl-ACP to 16- and 18-carbon fatty acids involves the cyclical action of the following sequence of reactions: condensation with a two-carbon unit from malonyl-ACP to form a β-ketoacyl-ACP (β-ketoayl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). Common plant unsaturated fatty acids, such as oleic, linoleic and a-linolenic acids found in storage triglycerides, originate from the desaturation of stearoyl-ACP to form oleoyl-ACP (C18:1) in a reaction catalyzed by a soluble plastid Δ-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound Δ-12 desaturase and Δ-15 desaturase. These "desaturases" thus create mono- or polyunsaturated fatty acids respectively.

A third β-ketoacyl-ACP synthase has been reported in *S. oleracea* leaves having activity specific toward very short acyl-ACPs. This acetoacyl-ACP synthase or "β-ketoacyl-ACP" synthase III has a preference to acetyl-CoA over acetyl-ACP, Jaworski, J. G., et al., *Plant Phys.* (1989) 90:41–44. It has been postulated that this enzyme may be an alternate pathway to begin FAS, instead of ATA.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of an enzyme source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful plant sources for nucleic acid sequences of such enzyme targets capable of modifying fatty acid compositions are needed. Ideally an enzyme target will be amenable to one or more applications alone or in combination with other nucleic acid sequences, relating to increased/decreased oil production, the ratio of saturated to unsaturated fatty acids in the fatty acid pool, and/or to novel oils compositions as a result of the modifications to the fatty acid pool. Once enzyme target(s) are identified and qualified, quantities of purified protein and purification protocols are needed for sequencing. Ultimately, useful nucleic acid constructs having the necessary elements to provide a phenotypic modification and plants containing such constructs are needed.

SUMMARY OF THE INVENTION

The present invention is directed to methods for producing plant oils having elevated levels of oleic acid (C18:1) as a percentage of the total fatty acids.

The method generally comprises growing a plant-containing a construct having as operably linked components in the 5' to 3' direction of transcription, a promoter region functional in a host plant cell, at least a portion of a nucleic acid sequence encoding a β-ketoacyl ACP synthase in an antisense orientation and a transcription termination sequence.

The methods described herein are utilized to produce plants with increased levels of oleic acid. Increases of at least 5 percent to 60 percent, preferably, 10 percent to 50 percent, more preferably 10 percent to 40 percent over the wild type seed oil are encompassed by the methods provided herein.

In one embodiment of the present invention, a Brassica seed oil having increased oleic acid is obtained using the methods of the present invention. The oleate content of the Brassica seed oil preferably comprises greater than 65%, more preferably greater than about 75% of the fatty acid moieties in the oil. The oil of the present invention may be used as a blending source to make a blended oil product, or it may also be used in the preparation of food.

In another embodiment of the present invention, a Brassica oil having a decreased polyunsaturated fatty acid composition is obtained using the methods described herein. Brassica oils with polyunsaturated fatty acid compositions of less than about 12 weight percent are exemplified herein.

BRIEF DESCRIPTION OF THE FIGURES

FIG. 1 The fatty acid composition from about 50 individual seeds from each of two lines of plants containing the construct pCGN3259.

DETAILED DESCRIPTION OF THE INVENTION

In accordance with the subject invention, constructs and methods are provided for the production of plants with an increased level of Oleic acid (C18:1), as a percentage of the total fatty acids. The methods for producing such plants generally comprise transforming a host plant cell with expression constructs having a promoter sequence functional in a plant operably associated to at least a portion of a nucleic acid sequence encoding a β-ketoacyl-ACP synthase (referred to herein as KAS) in an anti-sense orientation, and a transcription termination sequence. The expression constructs provide a novel method to increase in the levels of oleic acid in the seed oil of the transformed plants.

β-ketoacyl-ACP synthases are well known in the art for their involvement in the biosynthesis of fatty acids. The first step in the biosynthesis of fatty acids is the formation of acetyl-ACP (acyl carrier protein) from acetyl-CoA and ACP catalyzed by a short chain preferring condensing enzyme, β-ketoacyl-ACP synthase (KAS) III. Elongation of acetyl-ACP to 16- and 18-carbon fatty acids involves the cyclical action of the following sequence of reactions: condensation with a two-carbon unit from malonyl-ACP to form a longer β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I (KAS I), is primarily responsible for elongation up to palmitoyl-ACP (C16:0), whereas β-ketoacyl-ACP synthase II (KAS II) is predominantly responsible for the final elongation to stearoyl-ACP (C18:0).

Genes encoding peptide components of β-ketoacyl-ACP synthases I and II have been cloned from a number of higher plant species, including castor (*Ricinus communis*) and Brassica species (U.S. Pat. No. 5,510,255). KAS I activity was associated with a single synthase protein factor having an approximate molecular weight of 50 kD (synthase factor B) and KAS II activity was associated with a combination of two synthase protein factors, the 50 kD synthase factor B and a 46 kd protein designated synthase factor A. Cloning and sequence of a plant gene encoding a KAS III protein has been reported by Tai and Jaworski (*Plant Physiol.* (1993) 103:1361–1367).

Surprisingly, it is found herein that the antisense expression of at least a portion of a KAS I sequence in the seed cells of a host plant cell increases the oleic acid content of the seed oil.

Preferably, the KAS sequences used in the present invention are derived from the endogenous KAS sequence of the target host plant, also referred to herein as the native KAS sequence. The skilled artisan will recognize that also of use in the present invention are non-native KAS sequences obtained from sources other than the target host plant. By target host plant is meant the plant into which the expression constructs containing the KAS sequences are transformed.

As described in more detail in the examples that follow, a β-ketoacyl ACP synthase type I (referred to herein as KASI) coding sequence from Brassica (U.S. Pat. Nos. 5,475,099 and 5,510,255 the entireties of which are incorporated herein by reference) is used in expression constructs in an antisense orientation to generate transgenic Brassica plants with decreased production of the KASI in host cells.

Surprisingly, it is demonstrated herein that transformation of a plant with a construct providing antisense expression of the KASI gene leads to a significant increase in the levels of oleic acid (C18:1) obtained as a percentage of the total fatty acids produced in the seed oil. In addition, the transformed seeds demonstrate altered polyunsaturated fatty acid compositions as the result of the antisense KASI expression, such as seen in the decreases of linoleic (C18:2) and linolenic (C18:3) observed in the seed oil of plants containing elevated oleic acid.

Thus, using the methods of the invention, seeds are provided which produce an altered fatty acid composition and yield a vegetable oil which has increased oleic acid content and decreased linoleic and linolenic acid content. Thus, the transformed seed can provide a source of modified seed oil.

The constructs used in the methods of the present invention may also find use in plant genetic engineering applications in conjunction with plants containing elevated levels of oleate (18:1) fatty acids to further increase oleic acid levels. Such plants may be obtained by expression of stearoyl-ACP desaturase sequences, such as those sequences described by Knutzon et al. (*Proc. Nat. Acad. Sci.* (1992) 89:2624–2628). In addition, plants containing increased levels of oleic acid may be obtained by expressing nucleic acid sequences to suppress endogenous Δ12 desaturases. Such sequences are known in the art and are described in PCT Publication WO 94/11516. Increases in oleic acid may also be obtained by suppression of Δ12-desaturases and Δ-15 desaturases, such as the methods taught in U.S. Pat. No. 5,850,026. Plants producing elevated oleic acid content may also be obtained by conventional mutation and plant breeding programs.

Such methods for mutation are known in the art and are described, for example, in U.S. Pat. No. 5,625,130.

In addition, the constructs and methods for increasing oleic acid in seed oil may also find use in plant genetic engineering applications in conjunction with plants containing decreased levels of linoleate (C18:2) fatty acids and/or linolenate (18:3). Such plants with elevated levels of stearate and/or with decreased levels of linoleate and/or linolenate may be obtained through genetic engineering, or by conventional mutation and plant breeding programs. For example, methods for increasing stearate content of a seed oil are known in the art and are described for the use of a thioesterase from mangosteen (*Garcinia mangostana*), Garm FatA1 (Hawkins and Kridl (1998) *Plant Journal* 13(6):743–752; and PCT Patent Application WO 96/36719.

Furthermore, the constructs and methods for increasing oleic acid in seed oil may also find use in plant genetic engineering applications in conjunction with plants containing increased amounts of medium chain fatty acids to further increase the medium chain fatty acid content of the resulting plants. Such plants with elevated levels of medium chain fatty acids may be obtained through genetic engineering, or by conventional mutation and plant breeding programs. Methods for increasing medium chain fatty acids by genetic engineering are known in the art, and are described for example in U.S. Pat. Nos. 5,455,167 and 5,512,482 and in PCT Publication WO 98/46776.

Thus, recombinant constructs designed having the KASI sequence in a reverse orientation for expression of an anti-sense sequence or use of co-suppression, also known as "transwitch", constructs find use in the methods of the present invention. Antisense methods are well known in the art, and are described, for example, by van der Krol, et al. (1988) *Biotechniques* 6:958–976; Sheehy, et al. (1988) *Proc. Natl. Acad. Sci. USA* 85:8805–8809; Cannon, et al. (1990) *Plant Molec Biol.* 15:39–47. Methods for sense suppression are also well known in the art, and are described, for example, by Napoli et al. (1990) *Plant Cell* 2:279–289; van der Krol, et al. (1990) *Plant Cell* 2:291–299; and Smith, et al. (1990) *Mol. Gen. Genetics* 224:477–481.

Other methods for the suppression of native expression of target sequences are also known in the art, and include, but are not limited to, nucleic acid molecules with RNA cleaving activity, referred to as ribozymes (described in PCT Publication WO 97/10328), as well as combinations of antisense and sense suppression, such as that taught by Waterhouse, et al. (1998) *Proc. Natl. Acad. Sci. USA* 95:13959–13964. Thus, by suppression of the endogenous fatty acid biosynthesis system, for example by the methods of the present invention, a reduction in the amounts of phosphtidyl choline (also referred to as PC) may be obtained. Such reductions in PC result in a lower substrate level for further desaturases leading to increased amounts of mono-unsaturated fatty acids.

Sequences found in an anti-sense orientation may be found in cassettes which at least provide for transcription of the sequence encoding the synthase. By anti-sense is meant a DNA sequence in the 5' to 3' direction of transcription which encodes a sequence complementary to the sequence of interest. It is preferred that an "anti-sense synthase" be complementary to a plant synthase gene indigenous to the plant host. Any promoter capable of expression in a plant host which causes initiation of high levels of transcription in all storage tissues during seed development is sufficient. Seed specific promoters may be desired.

In preparing the expression constructs, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

For the most part, the constructs will involve regulatory regions functional in plants which provide for modified production of plant KAS I, and modification of the fatty acid composition. The open reading frame, coding for the plant KAS I or functional fragment thereof will be joined at its 5' end to a transcription initiation regulatory region such as the wild-type sequence naturally found 5' upstream to the thioesterase structural gene, or to a heterologous regulatory region from a gene naturally expressed in plant tissues. Examples of useful plant regulatory gene regions include those from T-DNA genes, such as nopaline or octopine synthase, plant virus genes, such as CaMV 35S, or from native plant genes.

For such applications when 5' upstream non-coding regions are obtained from other genes regulated during seed maturation, those preferentially expressed in plant embryo tissue, such as ACP, napin and β-conglycinin 7S subunit (Chen et al., (1986), *Proc. Natl. Acad. Sci.*, 83:8560–8564) transcription initiation control regions, as well as the Lesquerella hydroxylase promoter (described in Broun, et al. (1998) *Plant Journal* 13(2):201–210 and in U.S. patent application Ser. No. 08/898,038) and the stearoyl-ACP desaturase promoter (Slocombe, et al. (1994) *Plant Physiol.* 104:1167–1176), are desired. Such "seed-specific promoters" may be obtained and used in accordance with the teachings of U.S. Pat. No. 5,420,034 having a title "Seed-Specific Transcriptional Regulation" and in Chen et al., (1986), *Proc. Natl. Acad. Sci.*, 83:8560–8564. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant KAS I or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention. As described herein, transcription termination sequences derived from DNA sequences preferentially expressed in plant seed cells are employed in the expression constructs of the present invention.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium-mediated transformation. In addition, techniques of microinjection, DNA particle bombardment, and electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species in which the expression construct or components thereof are introduced, one or more markers may be employed, where different conditions for selection are used for the different hosts. A number of markers have been developed for use for selection of transformed plant cells, such as those which provide resistance to various antibiotics, herbicides, or the like. The particular marker employed is not essential to this invention, one or another marker being preferred depending on the particular host and the manner of construction.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Various methods of transforming cells of soybean have been previously described. Examples of soybean transformation methods have been described, for example, by Christou et al. U.S. Pat. No. 5,015,580 and by Hinchee et al. U.S. Pat. No. 5,416,011, the entireties of which are incorporated herein by reference.

Once a transgenic plant is obtained which is capable of producing seed having a modified fatty acid composition, traditional plant breeding techniques, including methods of mutagenesis, may be employed to further manipulate the fatty acid composition. Alternatively, additional foreign fatty acid modifying DNA sequence may be introduced via genetic engineering to further manipulate the fatty acid composition.

One may choose to provide for the transcription or transcription and translation of one or more other sequences of interest in concert with the expression of a plant stearoyl-ACP thioesterase in a plant host cell. In particular, the reduced expression of stearoyl-ACP desaturase in combination with expression of a plant stearoyl-ACP thioesterase may be preferred in some applications.

When one wishes to provide a plant transformed for the combined effect of more than one nucleic acid sequence of interest, typically a separate nucleic acid expression construct will be provided for each. The constructs, as described above contain transcriptional or transcriptional and translational regulatory control regions. The constructs may be introduced into the host cells by the same or different methods, including the introduction of such a trait by the inclusion of two transcription cassettes in a single transformation vector, the simultaneous transformation of two expression constructs, retransformation using plant tissue expressing one construct with an expression construct for the second gene, or by crossing transgenic plants via traditional plant breeding methods, so long as the resulting product is a plant having both characteristics integrated into its genome.

By decreasing the amount of stearoyl-ACP desaturase, an increased percentage of saturated fatty acids is provided. Using anti-sense, transwitch, ribozyme or some other stearoyl-ACP desaturase reducing technology, a decrease in the amount of β-ketoacyl-ACP synthase available to the plant cell is produced, resulting in a higher percentage of oleate fatty acids.

Of special interest is the production of triglycerides having increased levels of oleic acid. In addition, the production of a variety of ranges of oleate is desired. Thus, plant cells having lower and higher levels of oleate fatty acids produced by the methods described herein are contemplated. For example, fatty acid compositions, including oils, having a 65% level of oleate as well as compositions designed to have up to an approximate 78% level of oleate or other such modified fatty acid(s) composition are contemplated.

The seeds of the invention which have been transformed with the constructs providing antisense KASI expression provide a source for novel oil compositions. The use of such constructs, for example, results in substantial increases in oleic acid content in seed oil. By substantial increase is intended an increase of oleic acid to at least about 65% of the total fatty acid species. Thus, the seeds of the invention which have been transformed with a antisense KASI expression construct provide a source for modified oils having a high oleic acid content. The oleic acid content in any seed can be altered by the present methods, even those seeds having a naturally high oleic acid content. Alteration of seeds having naturally high oleic acid contents by the present methods can result in total oleic acid contents of as high as about 78%.

Importantly, there is also a decrease in linoleic and linolenic acid content. By decrease in linoleic fatty acid content is intended a decrease of the linoleic fatty acid species to less than about 15 mol percent of the total fatty acid species. By decrease in linolenic fatty acid content is intended a decrease in linolenic acid to about less than 7 mol percent of the total fatty acid content of the seed oil. Thus, the methods of the invention result in oils which are more oxidatively stable than the naturally occurring oils. The modified oils of the invention are low-saturate, high oleic and low linolenic. Furthermore, the present invention provides oils high in monounsaturated fatty acids which are important as a dietary constituent.

Based on the methods disclosed herein, seed oil can be modified to engineer an oil with a high oleic acid content. High oleic acid oils would have a longer shelf life as both the oleic acid content would lend to stability.

The methods of the present invention comprising the use of plant expression or transcription constructs having a plant β-ketoacyl-ACP synthase as the DNA sequence of interest may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, Cuphea, soybean, peanut, flax, coconut and oil palms, and corn. Depending on the method for introducing the recombinant constructs into the host cell, other DNA sequences may be required. Importantly, this invention is applicable to dicotyledon and monocotyledon species alike and will be readily applicable to new and/or improved transformation and regulation techniques.

The oil having increased oleic acid content may be processed using methods well known in the art. Furthermore, the processed oil having increased oleic acid produced by the methods of the present invention find use in a wide variety of end uses, such as edible as well as industrial uses. Such applications include, for example, salad oils, frying oils, cooking oils, spraying oils, and viscous-food product applications. The oil obtained according to the methods of the present invention, due to the increased monounsaturated fatty acid and the reduction in polyunsaturated fatty acid content, has a greater oxidative stability, thus reducing the need for chemical modifications, such as hydrogenation.

The invention now being generally described, it will be more readily understood by reference to the following examples which are included for purposes of illustration only and are not intended to limit the present invention.

EXAMPLES

Example 1
Expression Constructs

A construct containing the *Brassica campestris* synthase factor B (also referred to as KAS I) cDNA sequence (SEQ ID NO:1), pCGN3248 (described in U.S. Pat. No. 5,475,099, the entirety of which is incorporated herein by reference), is mutagenized to insert SmaI, BglII and SalI restriction sites approximately 200 bases 3' of the translation stop signal, resulting in pCGN3255. pCGN3255 is digested at the factor B cDNA internal SalI site located approximately 140 bases in from the 5' end of the cDNA and at the 3' BglII site inserted by mutagenesis. The resulting synthase factor B cDNA fragment is ligated into BglII and SalI digested pCGN3223, the above described napin expression cassette, resulting in antisense construct pCGN3257. Thus, transcription of the Brassica synthase factor B sequence from the napin promoter will result in production of an mRNA strand that is complementary to that of the endogenous Brassica synthase factor B gene.

The fragment containing the synthase gene in the expression cassette, 5' sequences/synthase/3' sequences, can be cloned into a binary vector such as described by McBride and Summerfelt (*Pl. Mol. Biol.* (1990) 14:269–276) for Agrobacterium transformation. Other binary vectors are known in the art and may also be used for synthase cassettes.

For example, the antisense Brassica synthase factor B construct in a napin expression cassette, pCGN3257 is digested with Asp 718 (same recognition sequence as KpnI) and cloned into Asp718 digested pCGN1578 (McBride and Summerfelt, supra) yielding binary construct pCGN3259.

Transformed *Brassica napus* plants containing the above described constructs are obtained as described in Radke et al. (*Theor. Appl. Genet.* (1988) 75:685–694 and *Plant Cell Reports* (1992) 11:499–505).

Example 2
Fatty Acid Analysis

The fatty acid composition is analyzed from about 50 individual seeds from each of two lines. The fatty acid compositions are shown in FIG. 1.

The results of the fatty acid compositional analysis demonstrates that significant increases in oleic acid (18:1) are obtained in the oil of Brassica seed containing antisense KAS I expression constructs. Oleic acid levels of as high as at least 78 mol percent are obtained using such constructs, for example in lines 3259-D12 (#100). Smaller increases are also obtained, for example several lines are obtained which contain over 70 mol percent oleic acid. Furthermore, the majority of the lines obtained contain greater than about 65 mol percent oleic acid.

Furthermore, reductions in the amount of polyunsaturated fatty acids are obtained in the oil of seeds from Brassica plants containing antisense KASI expression constructs. Amounts of linoleic acid is decreased to below 15% of the total fatty acid species, and as low as about 7.8 mol % in at least one seed of 3259-D-12. The linolenic acid content in the seeds of Brassica plants containing antisense KASI expression-constructs is reduced to less than about 6 mol percent, and in some lines linolenic acid content is reduced to about 5.1 mol percent. Total polyunsaturated fatty acid levels of less. than about 13 mol percent may be obtained using such constructs.

Example 3
Identification of Soybean β-ketoacyl-ACP Synthase I Sequences

In order to produce soybean lines with increased oleic acid content, additional KASI DNA sequences from soybean EST libraries are identified. Four EST sequences from soybean are identified which are related to the Brassica KASI sequence (U.S. Pat. No. 5,475,099) (SEQ ID NOs:2–5). Nine EST sequences are also identified in soybean EST libraries which are related to the Brassica KASII sequence (SEQ ID NO:6–14).

To obtain the entire coding region corresponding to the soybean KAS I EST sequences, synthetic oligo-nucleotide primers are designed to amplify the 5' and 3' ends partial cDNA clones containing acyltransferase related sequences. Primers are designed according to the respective soybean KAS I EST sequence and used in Rapid Amplification of cDNA Ends (RACE) reactions (Frohman et al. (1988) *Proc. Natl. Acad. Sci. USA* 85:8998–9002) using the Marathon cDNA amplification kit (Clontech Laboratories Inc, Palo Alto, Calif.).

Once a DNA sequence corresponding to the entire coding sequence, various portions of the sequence, or the entire coding sequence may be used to construct antisense expression vectors for use in transforming soybean plants using methods as provided for in the present invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for increasing the oleic acid content of a host plant cell comprising:
   growing a plant having an introduced nucleic acid construct, said construct comprising in the 5' to 3' direction of transcription, a promoter functional in a plant cell, a nucleic acid sequence encoding a β-ketoacyl-ACP synthase I protein, and a transcription termination region functional in a plant cell,
   whereby transcription of said nucleic acid sequence suppresses expression of the endogenous β-ketoacyl-ACP synthase I.

2. The method according to claim 1, wherein said nucleic acid sequence is in an antisense orientation with respect to said promoter.

3. The method according to claim 1, wherein said nucleic acid sequence is in a sense orientation with respect to said promoter.

4. The method of claim 1 wherein said nucleic acid sequence encoding a β-ketoacyl-ACP synthase I protein is obtained from the nucleic acid sequence encoding the endogenous β-ketoacyl-ACP synthase I of the host plant cell.

5. The method of claim 4, wherein said endogenous host plant is selected from the group consisting of: Brassica, soybean, and corn.

6. The method of claim 1 wherein said host plant cell is a seed cell.

7. A method for decreasing the polyunsaturated fatty acid content of a host plant cell comprising:
   growing a plant having an introduced nucleic acid construct, said construct comprising in the 5' to 3' direction of transcription, a promoter functional in a plant cell, a nucleic acid sequence encoding a β-ketoacyl-ACP synthase I protein, and a transcription termination region functional in a plant cell,
   whereby transcription of said nucleic acid sequence suppresses expression of the endogenous β-ketoacyl-ACP synthase I.

8. The method according to claim 7, wherein said nucleic acid sequence is in an antisense orientation with respect to said promoter.

9. The method according to claim 7, wherein said nucleic acid sequence is in a sense orientation with respect to said promoter.

10. The method of claim 7 wherein said nucleic acid sequence encoding a β-ketoacyl-ACP synthase I protein is obtained from the nucleic acid sequence encoding the endogenous β-ketoacyl-ACP synthase I of the host plant cell.

11. The method of claim 10 wherein said endogenous host plant is selected from the group consisting of: Brassica, soybean, and corn.

12. The method of claim 7 wherein said host plant cell is a seed cell.

13. The method according to claim 7 wherein said polyunsaturated fatty acid composition of the host plant cell is less than 13 mol percent.

* * * * *

SEQUENCE LISTING

<160> NUMBER OF SEQ ID NOS: 14

<210> SEQ ID NO 1

<211> LENGTH: 1573
<212> TYPE: DNA
<213> ORGANISM: Brassica sp.

<400> SEQUENCE: 1

| | | | | | |
|---|---|---|---|---|---|
| atgcgagaca | gcccacgaga | agacgctcat | tcatctccgc | gtcgtcctcc | gccgtctccg | 60 |
| cccccaaacg | cgaaacagac | ccgaagaaac | gggtcgtaat | caccggaatg | ggcctcgtct | 120 |
| ccgtcttcgg | aaacgacgtc | gacgcttact | acgagaagct | gctctccggc | gagagtggaa | 180 |
| tcagcttgat | tgatcggttc | gacgcctcca | agttcccgac | ccgattcggt | ggacagatcc | 240 |
| gtgggttcag | ctcagagggt | tacatcgatg | gaagaatga | gcggaggctt | gatgattgct | 300 |
| tgaagtactg | cattgtcgct | gggaagaagg | ctcttgaaag | tgcgaatctt | ggtggtgata | 360 |
| agcttaacac | gattgataag | cagaaagctg | gagtactagt | tgggactggt | atgggtggct | 420 |
| tgactgtgtt | ttcagacggt | gttcaagctc | ttattgagaa | aggtcacagg | aggatttctc | 480 |
| cttttctttat | tccttatgct | attacaaaca | tgggttctgc | tttgttggcg | attgatcttg | 540 |
| gtcttatggg | tcctaactac | tcgatctcga | cggcttgtgc | cacttctaac | tactgctttt | 600 |
| acgctgctgc | gaatcacatt | cgacgtggtg | aagctgatat | gatgatagct | ggtggaaccg | 660 |
| aggctgctat | tattcctatt | ggtttgggag | gttttgttgc | ttgtagggcg | ctttcacaga | 720 |
| gaaatgatga | tcctcagacg | gcttcaaggc | cgtgggataa | cagagagat | gggttttgtca | 780 |
| tgggtgaagg | agctggtgtt | ctggtgatgg | aaagcttgga | acatgcgatg | aaacgtggtg | 840 |
| ctccaattgt | agcagagtat | cttggaggcg | ctgttaactg | cgatgctcat | catatgactg | 900 |
| atccaagagc | tgatgggctt | ggtgtgtctt | catgcattga | gagctgcctt | gaagatgctg | 960 |
| gtgtatcacc | tgaggaggta | aattacatca | atgcacatg | aacttccaca | ctggctggtg | 1020 |
| atcttgctga | gattaatgcc | attaaaaagg | tattcaaaag | cacttcaggg | atcaaaatca | 1080 |
| atgccaccaa | gtctatgata | ggtcactgcc | tcggtgcagc | tggaggtctt | gaagccattg | 1140 |
| ccaccgtgaa | ggctatcaac | acgggatggc | tgcatccctc | tatcaaccaa | tttaacccag | 1200 |
| aaccagcagt | ggactttgat | acggtcgcaa | acgagaagaa | gcagcatgag | gtgaatgttg | 1260 |
| ccatatcaaa | ctcgtttggg | ttcggtggac | ataactcagt | ggtcgctttc | tctgccttca | 1320 |
| aaccctgatt | tcctcagacc | ctttagatcc | tctggtccat | ctgttagatc | accaccatca | 1380 |
| tcttcttcgc | agcttcttgg | ttcacaagtt | gagcgctttc | ttcctttcag | cttttttgttc | 1440 |
| ttattggtca | ttgttaattt | ttgctcaact | cttattggtc | attgaggtgt | agagaatcca | 1500 |
| gattttgctt | ctacaatctg | tgtacggaat | gttgtatctt | tagttcgttt | tatgtttgcc | 1560 |
| aaattttata | aac | | | | | 1573 |

<210> SEQ ID NO 2
<211> LENGTH: 282
<212> TYPE: DNA
<213> ORGANISM: Glycine max

<400> SEQUENCE: 2

| | | | | | |
|---|---|---|---|---|---|
| ggattcatgg | gtcccaacta | ctctatatcc | acggcttgtg | ctacttccaa | ttattgcttt | 60 |
| tatgctgcgg | cgaaccatat | tcggagaggg | gaggctgatt | tgatgatagc | cggtgggact | 120 |
| gaggctgcca | ttattcctat | tgggttaggg | ggttttgttg | cttgcagagc | gctttctcag | 180 |
| aggaacgacg | accctaaaac | cgcttccagg | ccatgggata | aggaacgtga | tggctttgtt | 240 |
| atgggtgaag | gtgctggagt | tttggtaatg | gagagcttgg | ag | | 282 |

```
<210> SEQ ID NO 3
<211> LENGTH: 269
<212> TYPE: DNA
<213> ORGANISM: Glycine max
<220> FEATURE:
<221> NAME/KEY: misc_feature
<222> LOCATION: (1)...(269)
<223> OTHER INFORMATION: n = A,T,C or G

<400> SEQUENCE: 3
gcagatggac aaaacaagaa taggagttct ggngggatca ggaatgggag gtataacggc      60
tttctcgaat ggtgtggaag ctcttgtaca aaagggatat aagaaaatta ctccattttt     120
cattccctac tccatcacca acatgggttc tgccttgttg gctatagaca caggcctaat     180
gggtcccaat tattcaattt ccactgcttg tgcaacggca aattactgct tttgtgcggc     240
tgctaatcac attagaaaag gcgaanaga                                        269

<210> SEQ ID NO 4
<211> LENGTH: 268
<212> TYPE: DNA
<213> ORGANISM: Glycine max
<220> FEATURE:
<221> NAME/KEY: misc_feature
<222> LOCATION: (1)...(268)
<223> OTHER INFORMATION: n = A,T,C or G

<400> SEQUENCE: 4
agcttctcgc cggcgagagc ggcatcaccc ccatcgaccg cttcgacgcc tccaagtttc      60
ccacgcgctt cggcggccag atccgcggct tctccgccga gggctacatc gacggcaaga     120
acgaccgccg cctcgacgac tgcctccgct actgcattgt cgccggcaaa aaggccctcg     180
aaaacgccga ccttccccag acaaccactc caagagtgac naggagcgtn cngnngtcct     240
tnnggcncgg aantggaggg ttnacggg                                         268

<210> SEQ ID NO 5
<211> LENGTH: 279
<212> TYPE: DNA
<213> ORGANISM: Glycine max
<220> FEATURE:
<221> NAME/KEY: misc_feature
<222> LOCATION: (1)...(279)
<223> OTHER INFORMATION: n = A,T,C or G

<400> SEQUENCE: 5
ataaggagcg tgctggtgtt cttgnaggnt ctggaatggg aggcttaacg ntgttgtctt      60
cacggtgnnn agnctctnnt tcannagggg cacnggaagn taacgccgtt tcctcattcc     120
ttatgcaatt actaacatgg gttcggcttt gcttgggata naccttggat tcatgggtcc     180
aactactcta tatccacggc ttgtgctact tccaattatt gcttttatgc tgcggcgaac     240
catattcgga gagggaggc tgatttgatg atagccggc                              279

<210> SEQ ID NO 6
<211> LENGTH: 289
<212> TYPE: DNA
<213> ORGANISM: Glycine max
<220> FEATURE:
<221> NAME/KEY: misc_feature
<222> LOCATION: (1)...(289)
<223> OTHER INFORMATION: n = A,T,C or G

<400> SEQUENCE: 6
ggagcatgct aaggaaagag gtgcaaccat atatgctgaa ttccttggtg gaagtttcac      60
```

```
ctgtgatgca tatcatgtga ctgagccgcg tcctgatggg gctggtgtta tactgtgcat      120
tgaaaaggca ttagctcagt ctggagtatc aaaagaggat gtgaattaca tanatgcaca      180
tgccacatcc acaccagctg gagatcttaa ggagtaccaa gctctaatgc attgttttgg      240
tcaaaacccc gagttaagag tgaattctac aaaatctatg attggtcat                  289
```

<210> SEQ ID NO 7
<211> LENGTH: 248
<212> TYPE: DNA
<213> ORGANISM: Glycine max
<220> FEATURE:
<221> NAME/KEY: misc_feature
<222> LOCATION: (1)...(248)
<223> OTHER INFORMATION: n = A,T,C or G

<400> SEQUENCE: 7

```
gtggcatgaa ggttttcaat gatgccatcg aagctttacg aatctcatat aagaagatga      60
atcctttttg tgtaccttt gcnacaacaa atatgggttc tgccatgctt gcnatggatc       120
tgggatggat gggccctaat tattctatct ctacagcttg tgctacaagt aacttttgta      180
tattgaatgc agcaaaccat atcattagag gtgaagctga tgtgatgctt tgtggaggct      240
cagatgct                                                               248
```

<210> SEQ ID NO 8
<211> LENGTH: 267
<212> TYPE: DNA
<213> ORGANISM: Glycine max
<220> FEATURE:
<221> NAME/KEY: misc_feature
<222> LOCATION: (1)...(267)
<223> OTHER INFORMATION: n = A,T,C or G

<400> SEQUENCE: 8

```
gcatatcatg tgactgagcc gcgtcctgat ggggctggtg ttattctttg cattgaaang      60
gcattagctc agtctggagt atcaaaagag gatgtgaatt acataaatgc acatgccaca      120
tccacaccag ctgagatct taaggagtac caagctctaa tgcattgttt tggtcaaaac       180
cccaagttac gagtgaattc tacaaaatct atgattggtc atctactagg ggcagctggc      240
gctgtggaag ctgtggccac aatacag                                          267
```

<210> SEQ ID NO 9
<211> LENGTH: 341
<212> TYPE: DNA
<213> ORGANISM: Glycine max
<220> FEATURE:
<221> NAME/KEY: misc_feature
<222> LOCATION: (1)...(341)
<223> OTHER INFORMATION: n = A,T,C or G

<400> SEQUENCE: 9

```
agctctaatg cattgttttg gtcaaaaccc cgagttaaga gtgaattcta caaatctat       60 gattggtcat ctactagggg cagctggcgg tgtggaagct gtggccacaa tacaggcaat      120
tagganaggg tgggttcatc ccaatatcaa cctagaaaac ccagataacg gagtggatgc      180
taaagtgctt gttggctcaa agaaagagag actggatgtc aaggcagcct tgtcgaattc      240
atttggtttt ggggtcaca attcntcaat catatttgca ccatactagt gaaacagatt       300
tcagagcagt acntncttat tattataagt tactgagtan c                          341
```

<210> SEQ ID NO 10
<211> LENGTH: 191

```
<212> TYPE: DNA
<213> ORGANISM: Glycine max
<220> FEATURE:
<221> NAME/KEY: misc_feature
<222> LOCATION: (1)...(191)
<223> OTHER INFORMATION: n = A,T,C or G

<400> SEQUENCE: 10
gcagaatatc caacaaggat tgcnggtgaa atcaagtctt tctcaactga tggctgggta      60
gcaccaaaac tttctaagag aatggataaa tttatgctct atatgctgac agctggcaaa     120
aaagccttgg ttgatggtgg aattactgat gatgtaatgg atgagtnaaa taangaaaag     180
tgtggagttc t                                                          191

<210> SEQ ID NO 11
<211> LENGTH: 281
<212> TYPE: DNA
<213> ORGANISM: Glycine max
<220> FEATURE:
<221> NAME/KEY: misc_feature
<222> LOCATION: (1)...(281)
<223> OTHER INFORMATION: n = A,T,C or G

<400> SEQUENCE: 11
ccatatcatt agaggtgnag ctgatgtgat gctttgtgga ggctcagatg ctgctatnat      60
accaattggt ttgggaggct tgtggcatg caggcactc tcacaaagga atantgatcc      120
taccaaagcn tcangccttg ggactnaanc gtgatggatt tgtcannggt gaagggcttg     180
cagtctgccn gtagaggaac tngagcatgc caaggaaaga gngtgcaaca tatatgnngn     240
atcctggtgg aagtttcacc tgtgatgcat atcatgtnat g                        281

<210> SEQ ID NO 12
<211> LENGTH: 267
<212> TYPE: DNA
<213> ORGANISM: Glycine max

<400> SEQUENCE: 12
ggcggtgtgg aagctgtggc cacaatacag gcaattagga cagggtgggt tcatcccaat      60
atcaacctag aaaacccaga taacggagtg gatgctaaag tgcttgttgg ctcaaagaaa     120
gagagactgg atgtcaaggc agccttgtcg aattcatttg gttttggggg tcacaattct     180
tcaatcatat ttgcaccata ctagtgaaac agatttcaga gcagtacttt cttattatta     240
taagttactg agtacccaga caatgtt                                         267

<210> SEQ ID NO 13
<211> LENGTH: 282
<212> TYPE: DNA
<213> ORGANISM: Glycine max
<220> FEATURE:
<221> NAME/KEY: misc_feature
<222> LOCATION: (1)...(282)
<223> OTHER INFORMATION: n = A,T,C or G

<400> SEQUENCE: 13
gctgatgtga tgctttgtgg aggctcagat gctgctatta ccaattggt tttgggaggc       60 tttgtggcat gcagggcact ctcacaaagg aatactgatc ctaccaaagc ttcacgccct     120
tgggacatta accgtgatgg atttgtcatg ggtgaagggg ctggagtttt gcttttagag     180
gaactggagc atgctaagga aagaggtgca ancatatatg ctgaattcct tggtggatttt    240 cacctgtgaa gcctatcatg tggactgagc cgcgtcctga tg                        282
```

-continued

```
<210> SEQ ID NO 14
<211> LENGTH: 276
<212> TYPE: DNA
<213> ORGANISM: Glycine max

<400> SEQUENCE: 14
accgtgatgg atttttcatg ggtgaagggg ctggagtttt gcttttagag gaactggagc      60
atgctaagga aagaggtgca accatatatg ctgaattcct tggtggaagt ttcacctgtg     120
atgcatatca tgtgactgag ccggtcctga tggggctggt gttatactgt gcattgaaaa     180
ggcattagct cagtctggag tatcaaaaga ggatgtgaat tacataaatg cacatgccac     240
atccacacca gctggagatc taaggagtac caagcc                               276
```